United States Patent [19]
Koewler

[11] Patent Number: 5,476,489
[45] Date of Patent: Dec. 19, 1995

[54] COLD THERAPY SYSTEM

[75] Inventor: Danial E. Koewler, Batavia, Ohio

[73] Assignee: Seabrook Medical Systems, Inc., Cincinnati, Ohio

[21] Appl. No.: 188,962

[22] Filed: Jan. 28, 1994

[51] Int. Cl.$^6$ ............................................. A61F 7/00
[52] U.S. Cl. ............................................. 607/104; 607/114
[58] Field of Search ............................ 607/96, 108–112, 607/114

[56] References Cited

U.S. PATENT DOCUMENTS

| | | | |
|---|---|---|---|
| 2,726,658 | 12/1955 | Chessey | 607/104 |
| 3,477,427 | 11/1969 | Lapidus | 607/104 X |
| 3,918,458 | 11/1975 | Nethery | 607/104 |
| 4,112,943 | 9/1978 | Adams | 607/104 X |
| 4,459,468 | 7/1984 | Bailey | 607/104 X |
| 4,821,354 | 4/1989 | Little | 607/104 X |
| 4,960,103 | 10/1990 | Urso | 607/104 X |
| 5,174,285 | 12/1992 | Fontenot | 607/104 |
| 5,241,958 | 9/1993 | Noeldner | 607/104 X |

Primary Examiner—Angela D. Sykes
Attorney, Agent, or Firm—Frost & Jacobs

[57] ABSTRACT

A cold therapy system for appyling a cooling pad to an area of the body of the user. The system comprises a portable insulated cooler with a lid. A reservoir bag of plyable waterproof material is locatable within said cooler and has a closable open top for the introduction of water and ice into the bag. A multispeed pump is located in a housing affixed to the exterior of the cooler. The pump has an inlet operatively connected to an outlet tubing flange affixed to the bag. The pump has an outlet operatively connected to an insulated delivery tube connected to an inlet of the pad. The outlet of the pad is connected by an insulated return tube to an inlet flange of the reservoir bag. A portion of the insulation of one of the delivery and return tubes, is retractable to expose a segment of its respective tube containing a liquid crystal temperature indicator for determining the temperature of the fluid flowing through the system.

5 Claims, 6 Drawing Sheets

COLD THERAPY SYSTEM

TECHNICAL FIELD

The invention relates to a cold therapy system of the type wherein cold water is circulated between a body contacting pad and a cooler by a pump and a delivery and return tube assembly, and more particularly to such a system wherein the cooler contains a pliable, water proof reservoir bag for water and ice; wherein the pump is located externally of the cooler; and wherein an in-line liquid crystal temperature indicator is located within a tube of the delivery and return tube assembly.

BACKGROUND ART

There are a number of instances, inclusive of injuries, surgery and the like, for which cold therapy is prescribed. To this end, water proof pads have been devised in various sizes and shapes to be applied against or wrapped about a body part to be treated. Each pad has an inlet and an outlet and a path within the pad extending between the inlet and the outlet through which cold water is filled and removed from the pad or circulated through the pad.

In recent years there has been a marked increase in sports activities, for example, and a marked increase in a number of people participating therein. As a result, there has been an increased demand for a simple, portable, cold therapy system, capable of use in the home or elsewhere. It will further be understood that the use of such systems is not limited to sports injuries.

Prior art workers have devised a number of cold therapy systems in an attempt to meet this demand. One approach is to provide a pad for application to the body area to be treated, a cooler filled with ice and water, and a tube extending from the cooler to the pad. The cooler is held above the pad so that chilled water is introduced into the pad from the cooler by gravity. As the chilled water in the pad warms from body heat, the cooler can be placed in a position below the pad, causing the pad to drain into the cooler. After a short time the water is recooled by the ice in the cooler and the process may be repeated. Such a system requires considerable manipulation by the user, and does not provide an even cold temperature at the treatment site.

Recently, a number of prior an workers have devised cold therapy systems wherein cold water is continuously circulated through a pad by means of a pump. An example of such a system is taught in U.S. Pat. No. 5,241,951.

In prior an systems utilizing a pump, it is usual that the pump is submerged in a reservoir of water and ice or pre-frozen ice units. Such systems generally require a rather large amount of water with respect to the amount of ice used. They again require a fair amount of set-up by the user and are subject to spillage. Since the pump is located within the reservoir of water and ice, heat generated by the pump directly affects the chilled water reservoir.

The present invention is directed to a cold therapy system which overcomes a number of the deficiences of prior art systems. According to the present invention, a reservoir for water and ice is provided in the form of a flexible, waterproof, open-top bag. The open top may be rolled to a closed condition and maintained therein by a drawstring. The reservoir bag is located in a standard cooler having a closure lid. This approach greatly reduces the chances of spillage and air space between the cooler and the reservoir bag further contribute to the insulation of the bag from ambient temperature. The reservoir bag is connected to a treatment pad through a pump and an insulated delivery tube. The pad is connected by an insulated return tube to the reservoir bag. The pump is mounted in a housing affixed to the exterior of the cooler so that the ice and water are isolated from any heat generated by the pump.

The pump of the present invention is a multi-speed design, enabling control of the water temperature returning from the pad by means of flow rate, eliminating the need for restrictive valves or the like. The system requires a minimum of water, allowing the use of more ice. This not only further reduces the chances of spillage, but also enables the treatment time to be extended. Finally, the system is provided with a liquid crystal temperature indicator located in the return line.

DISCLOSURE OF THE INVENTION

According to the invention there is provided a cold therapy system for applying a cooling pad to an area of the body of the user. The system comprises a portable insulated cooler having a lid. A reservoir bag of pliable, waterproof material is located within the cooler and is provided with an open top for the receipt of water and ice. The open top of the reservoir bag is closable and means are provided to maintain it in closed position. A pump is located within a housing affixed to the exterior of the cooler. The pump has an inlet operatively connected through the adjacent cooler wall to an outlet port of the reservoir bag. The pump has an outlet connected by means of an insulated delivery tube to the inlet of the pad. The outlet of the pad is connected by an insulated return tube, through the cooler wall through which the pump housing is affixed, to an inlet of the reservoir bag.

The pump is a multi-speed pump enabling regulation of the rate of flow within the system, and therefore, the treatment provided by the pad. A liquid crystal temperature indicator is located within one of the delivery and return tubes. The insulation of that tube having the temperature indicator therein is retractable, enabling the reading of the temperature indicator.

DETAILED DESCRIPTION OF THE INVENTION

Figure 1:
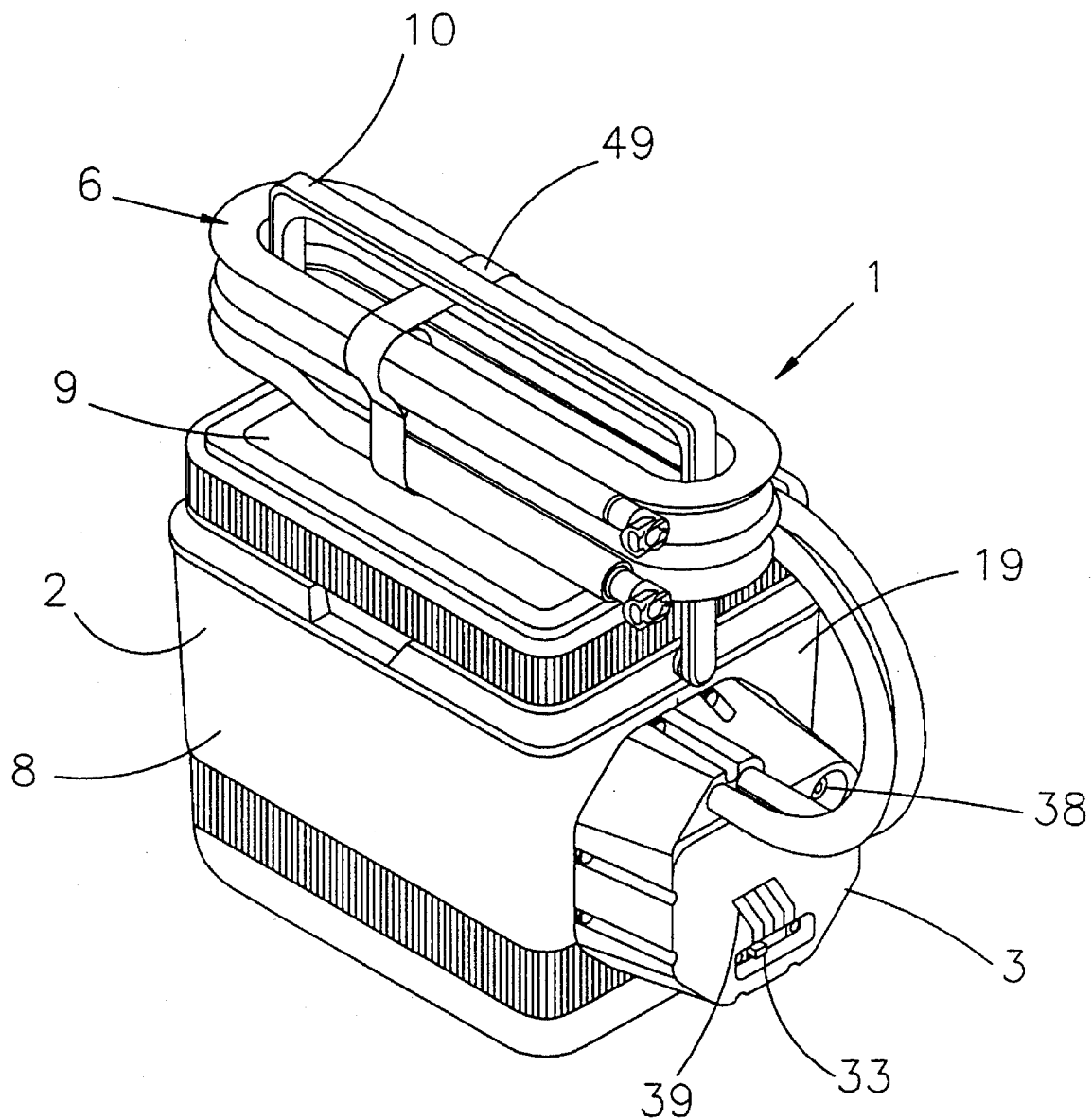
FIG. 1 is a perspective view illustrating the cooler, the pump housing, and the tube assembly of the cold therapy system of the present invention.
Figure 2:
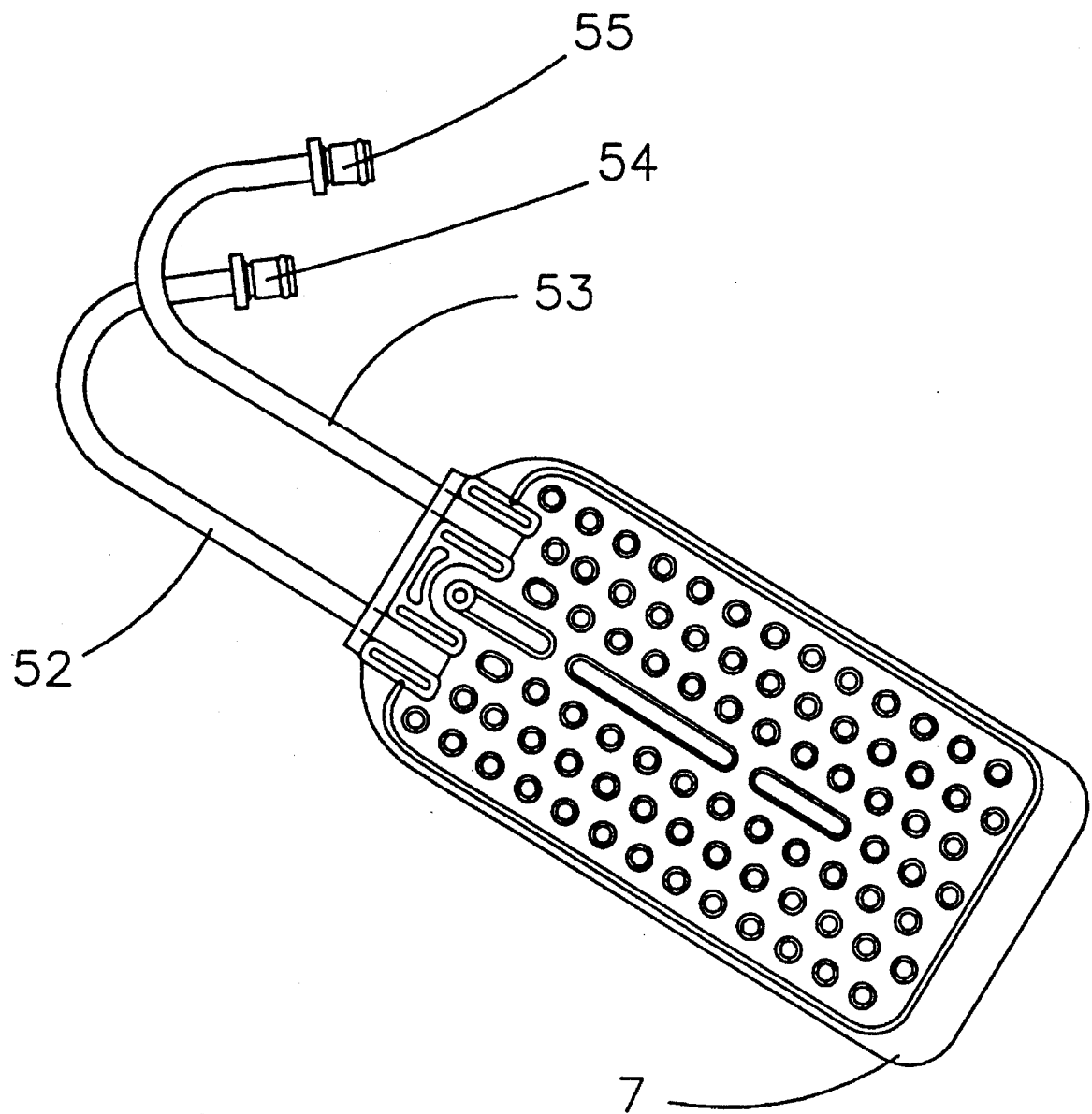
FIG. 2 is a perspective view illustrating an exemplary pad for use with the cold therapy system of the present invention.

Throughout the Figures, like parts are given like index numerals. Reference is first made to FIGS. 1 and 2. In FIG. 1, the overall cold therapy system of the present invention is generally indicated at 1. The system comprises a portable cooler 2 which contains a reservoir of water and ice (not shown in FIG. 1). The cooler 2 has an exterior housing 3 affixed to one of its ends. The housing 3 contains a pump 4 and a pump control means 5 (see FIG. 4). The pump and reservoir are connected to a cooling pad 7 (shown in FIG. 2) by a return and delivery tube assembly, generally indicated at 6. As will be understood by one skilled in the art, the cooling pad may be placed against or wrapped about that part of the user requiring cold therapy.

Figure 3:
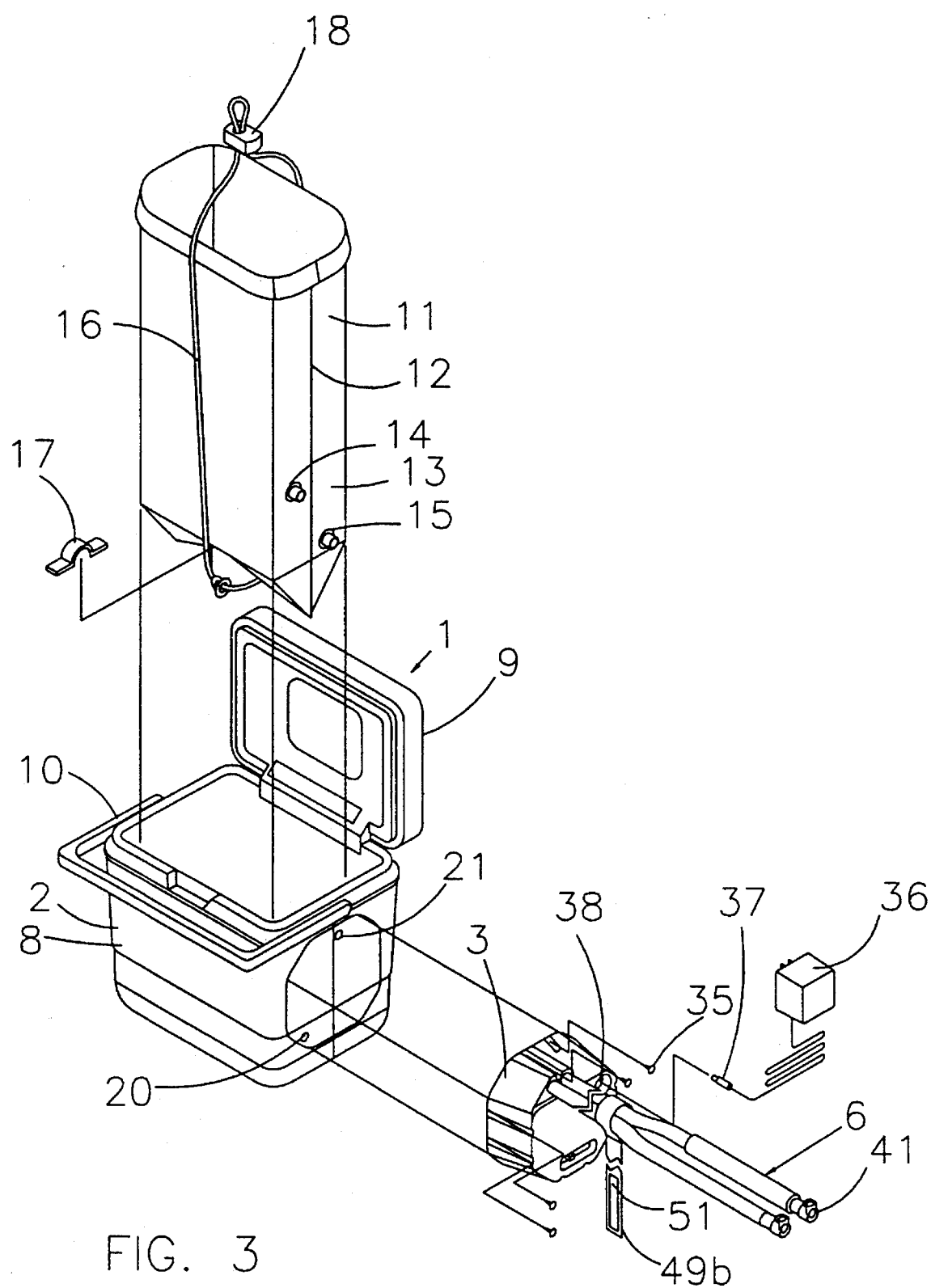
FIG. 3 is a fragmentary, exploded, perspective view of the cold therapy system of the present invention.

Each of the elements broadly set forth above, will now be described in detail. Referring to FIG. 3, the cooler 2 may be any appropriate conventional cooler having an insulative body 8 and an insulative lid 9. While it may be a separate element, the lid 9 is preferably hinged to the cooler body 8, and preferably makes a reasonably good sealing closure with the open top of body 8 so that the insulative qualities of the cooler are not compromised. The cooler 2 may have a bail-type handle 10, as is well known in the art. An example of a portable insulative cooler suitable for this purpose is manufactured by Gott Corporation of Winfield, Kans., under the model designation 1910.

Locatable within cooler 2 is an open top bag 11 made of pliable, waterproof, plastic material. Excellent results have been achieved, for example, with a bag made of 8 gauge clear vinyl. The bag 11 may be made in any appropriate manner. In an exemplary embodiment, a sheet of clear vinyl was folded upon itself and the edges of the open bottom and open side were joined together by radio frequency welding. The side welding seam is shown in FIG. 3 at 12. One end 13 of the bag 11 is provided with a pair of perforations through which straight tubing flanges 14 and 15 extend. The straight tubing flanges 14 and 15 may be affixed to bag 11 in any appropriate manner, including radio frequency welding or the like. Flange 14 comprises and outlet flange and flange 15 comprises an inlet flange, as will be apparent hereinafter.

The bag 11 is so sized as to fit nicely within the body 8 of cooler 2. The bag 11 is surrounded by a drawstring 16 of polyester or other appropriate material. The drawstring may pass beneath a retrainer strap 17 adhesively affixed to the inside surface of the bottom of cooler 2. The upper end of drawstring 16 may be provided with a slide cord lock 18. In use, the bag 11 is filed with ice and water and the open top of the bag is rolled downwardly to close it. The drawstring 16, through the agency of slide cord lock 18, is tightened about the bag to maintain its upper end in rolled and closed condition.

It will be noted that the straight tubing flanges 14 and 15 of bag 11 are staggered. The tubing flange 15 being higher than the tubing flange 14. The cooler body 8 has an end 19 provided with a pair of perforations 20 and 21. The perforations 20 and 21 extend through the cooler body end 19 and roughly correspond in placement to the positions of the bag tubing flanges 14 and 15.

Figure 4:
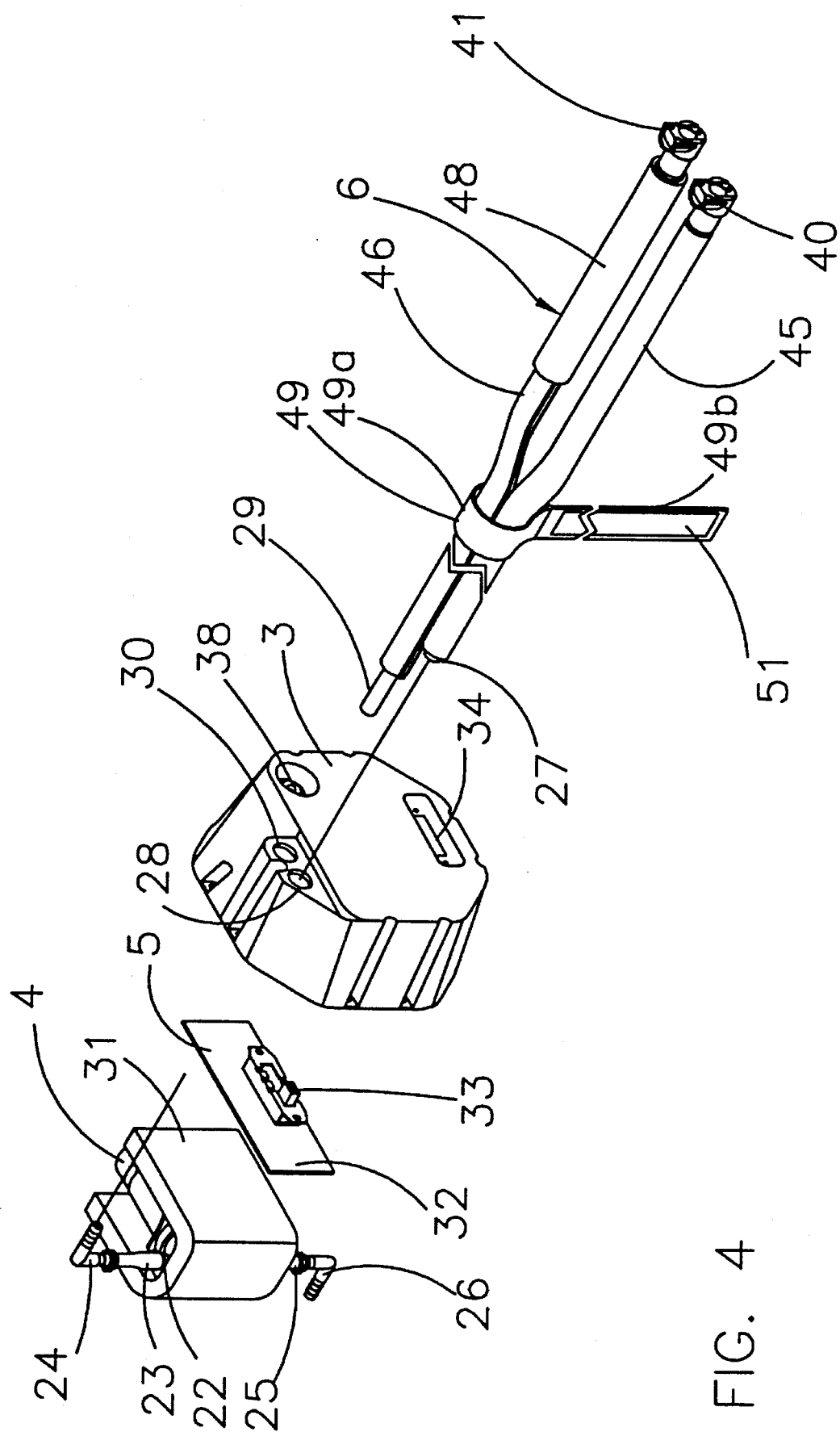
FIG. 4 is a fragmentary, exploded, perspective view illustrating the pump, the pump housing, the control circuit board and switch, and the tube assembly of the present invention.

Reference is now made to FIGS. 3 and 4. The pump 4 includes, as a part thereof, a variable speed motor. The pump has a tubular inlet port (not shown) and a tubular outlet port 22. It will be understood that the inlet port in substantially identical to outlet port 22. Outlet port 22 is connected by means of a short piece of gum rubber tubing 23 to a connector elbow 24. The inlet of pump 4 is similarly connected by a short piece of gum rubber tubing 25 to a connector elbow 26. While not necessarily intended to be limiting, in an exemplary embodiment of the cold therapy system of the present system, all tubing used had an internal diameter of ¼ inch. In the particular embodiment, the pump 4 had tubular inlet and outlet members having an inside diameter of ⅜ inch. The soft, stretchable, gum rubber tube segments 23 and 25 enabled connection between the ⅜ inch pump inlet and outlet elements and the ¼ inch elbow connectors 24 and 26. In addition to enabling these connections, the soft gum rubber tube segments 23 and 25 contributed to the quiet operation of the pump. In an instance where the tubular pump inlet and outlet members and the elbow connectors 24 and 26 have the same outside diameter, PVC tubing may be used throughout, if desired. The pump inlet elbow connector 26 is further connected by a tube segment (not shown) to the outlet tubing flange 14 of bag 11. The outlet elbow connector 24 of pump 4 is connected to a delivery tube 27. Delivery tube 27 passes through a perforation 28 in pump housing 3. A return tube 29 passes through a perforation 30 in pump housing 3. Return tube 29 also passes through the perforation 20 in the cooler body end 19, and is connected to the inlet tubing flange 15 of reservoir bag 11.

The pump 4 is preferably a positive displacement pump, easy to prime and capable of operating at multiple speeds (i.e., low, medium and high). Excellent results have been achieved utilizing a pump manufactured by Surflow, of Garden Grove, Calif., and having the Model No. 100-000-20. In the exemplary embodiment described, the pump 4 provides approximately 8 gallons per hour (8 gph) of liquid flow at the high speed mode of operation, about 5 gallons per hour (5 gph) at medium speed, and about 3 gallons per hour (3 gph) at low speed.

The pump 4 has wrapped thereabout a piece 31 of foamed material. The foamed material 31 serves several purposes. First of all, it separates the pump 4 from pump housing 3 and the end 19 of cooler body 8. As a consequence, the pump 4 is essentially free floating within pump housing 3 tending to reduce noise and vibration. Foamed material 31 also acts as an insulator for both heat and noise from the pump. The pump is supported within pump housing 3 by foamed material 31 and the connections to its inlet and outlet ports.

The pump control means 5 comprises a circuit board 32 including a four position manual switch 33. The pump control means 5 is preferably of the type described in co-pending application Ser. No. 08/128,303, filed Sep. 28, 1993 in the name of Norman D. Neal, and entitled PULSE-WIDTH MODULATING CONTROLLER. The teachings of this copending application are incorporated herein by reference. The switch portion 33 of the pump control means 5 is provided with lateral flanges which are riveted or otherwise appropriately affixed to the inside front surface of pump housing 3. The pump housing 3 is provided with a transverse slot 34 through which the manual actuator of switch 33 extends.

With the pump control means 5 affixed thereto, and the pump 4 located therein, the pump housing is mounted on the end 19 of the cooler body 8 by a plurality of self-tapping screws 35. The motor portion of pump 4 constitutes a 12-volt DC motor and is connected to a source of power through the pump control means 5. The power source may be a battery, or it may be a 12-volt power supply, as shown at 36 in FIG. 3. Power supply 36 may be connected to any conventional household outlet, or the like, and is provided with a jack 37 receivable within a socket 38 in pump housing 3. The socket 38 is appropriately connected to the pump control means 5. It is within the scope of the invention to provide indicia on the front face of the pump housing to indicate the position of the manual actuator of switch 33. Such indicia is suggested at 39 in FIG. 1. The indicia may be coded coated and may be provided with legends reading from left to right in FIG. 1 as follows: "STOP", "HIGH", "MEDIUM", and "LOW". Alternatively, they may read from left to right as follows: "STOP", "COLDEST", "COLD", and "COOL".

Figure 5:
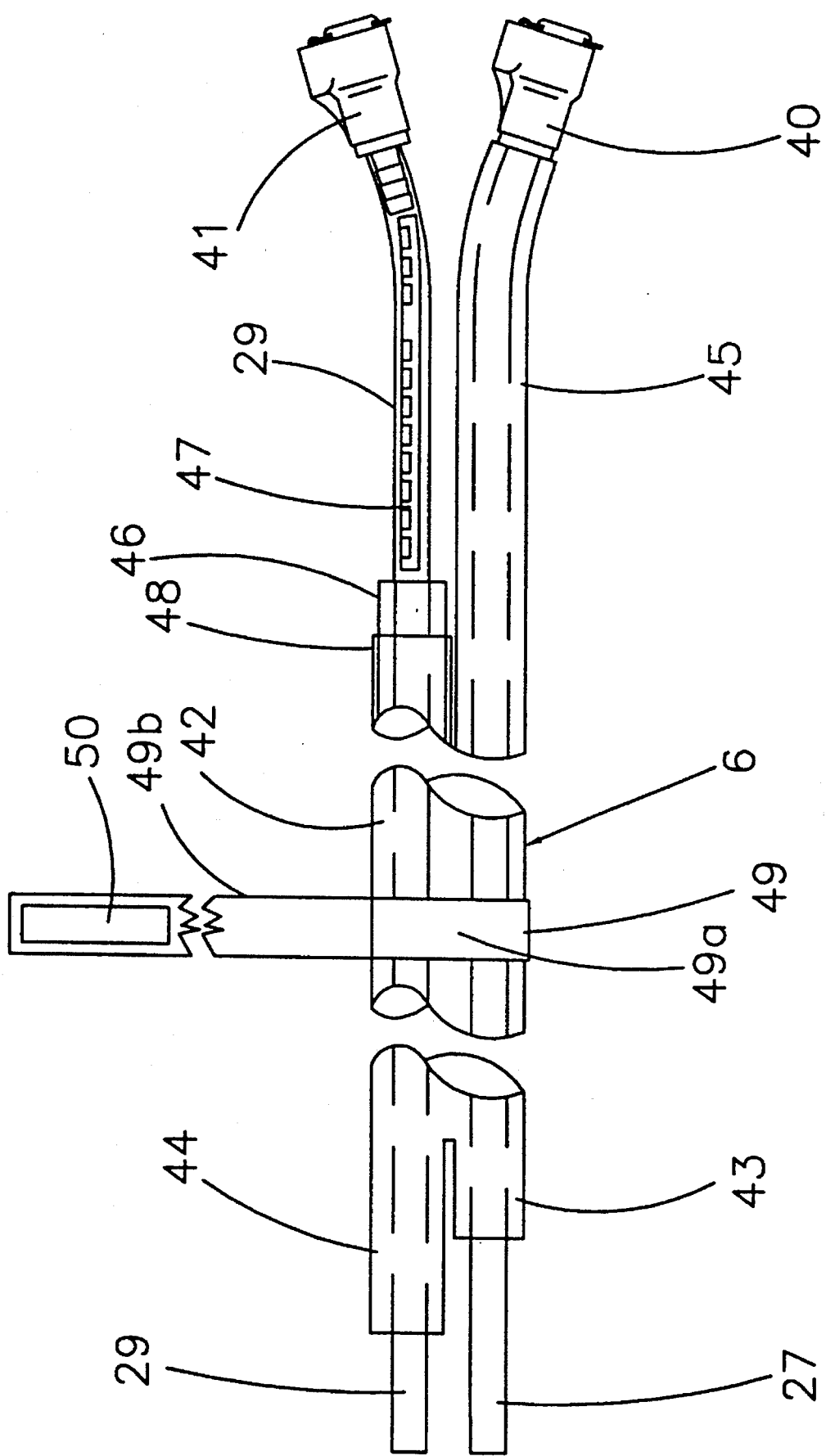
FIG. 5 is a fragmentary elevational view of the tube assembly of the present invention.

As indicated above, the outlet elbow 24 of pump 4 is connected to a delivery tube 27 which extends through perforation 28 in pump housing 3. A return tube 29 extends through a perforation 30 in the pump housing 3 and the perforation 21 in the end 19 of cooler body 8, and is connected to the inlet tubing flange 15 of reservoir bag 11. Delivery and return tubes 27 and 29 constitute the tube assembly 6, and are best shown in FIG. 5.

In an exemplary embodiment, the delivery and return tubes 27 and 29 comprised PVC tubing having a ¼ inch internal diameter. At their free ends, delivery and return tubes 27 and 29 are provided respectively with female quick disconnect tube couplings 40 and 41, respectively. The female couplings 40 and 41 are in-line couplings preferably of the type having shut-off means. Preferably, they are provided with shrouded release buttons to prevent accidental disconnects. Female couplings of this type are available, for example, from Colder Products Company of St. Paul, Minn., having a part number PLCD 170-04.

The delivery and return tubes 27 and 29 are provided substantially throughout their length with a foam tube insulation covering 42. The foam tube insulation 42 comprises two tubular members having an inside diameter to just nicely receive the delivery and return tubes 27 and 29 and which are joined together by a web located therebetween, so that the foam tube insulation comprises an integral, one-piece structure accommodating both the delivery and return tubes 27 and 29. Near its rearward end the foam tube insulation 42 is split into two separate end portions 43 and 44 so that they can enter perforations 28 and 30 of pump housing 3. This is shown in FIGS. 1 and 3. The foam tube insulation end portion 43 surrounding delivery tube 27 extends substantially to the joinder of delivery tube 27 to output elbow 24 of pump 4. The foam tube insulation end portion 44 surrounding return tube 29 extends substantially to the point where return tube 29 passes through perforation 21 in the end 19 of cooler body 8.

At its forward end, the foam tube insulation 42 is again split into two separate end portions 45 and 46. End portion 45, surrounding delivery tube 27, extends to the female coupling 40. End 46, on the other hand, terminates short of female coupling 41, exposing a length of return tube 29. The exposed portion of return tube 29 contains a liquid crystal temperature indicator, indicated in broken lines at 47. Temperature indicator 47 monitors and indicates the temperature of the water returning from pad 7 to reservoir bag 11. Liquid crystal in-line temperature indicators are available, for example, from Hallcrest of Glenview, Ill. The liquid temperature indicator 47 is held in place within return tube 29 by frictional engagement between temperature indicator 47 and the inside surface of return tube 29.

The forward end portions 45 and 46 of the foam tube insulation 42 are separated from each other for a distance sufficient to accommodate an additional length of foam tubing insulation 48. Insulative member 48 has an internal diameter of such size as to be slidable on foam tube insulation end portion 46 between a retracted position wherein it completely exposes temperature indicator 47 (as shown in FIG. 5), and a position wherein the forward end of insulative member 48 contacts female coupling 41, while the rearward end of insulative member 48 slightly overlaps the forwardmost end of foam tube insulation end portion 46. Thus, the insulative member 48 may be used to cover that portion of return tube 29 containing temperature indicator 47 between readings thereof. As will be understood by one skilled in the art, the temperature indicator 47 and its slidable insulative member 48 could have been provided in association with delivery tube 27, if desired.

The tubing assembly 6 is completed by a storage strap 49. Storage strap 49 has a portion 49a which extends about tube assembly 6. Storage strap 49 has a laterally extending portion 49b. One side of storage strap portion 49b has affixed thereto one part of a hook and loop tape assembly, as indicated at 50 in FIG. 5. The other side of the portion 49b of storage strap 49 has affixed thereto the other part of the hook and loop assembly, as indicated at 51 in FIG. 4. The storage strap 49 enables the tube assembly 6 to be coiled and maintained in a coiled position. Preferably, the tube assembly 6 is coiled about the cooler handle 10 and is maintained in this position by storage strap 49, as shown in FIG. 1.

The cold therapy system of the present invention is completed by the provision of cooling pad 7. Cooling pad 7 is conventional and may be of any appropriate size or shape. The cooling pad 7 is normally made up of a pair of waterproof plastic plies joined together so as to form a tortuous path for the chilled water entering and leaving the pad. For this purpose, the pad is provided with a delivery tube 52 and a return tube 53. The delivery and return tubes 52 and 53 may comprise ¼ inch PVC tubing. One end of each of delivery and return tubes 52 and 53 is attached to cooling pad 7. The other end of each of delivery and return tubes 52 and 53 are provided with straight through male couplings adapted to cooperate with female couplings 40 and 41 (see FIG. 5). Such straight through male couplers are available, for example, from Colder Products Company of St. Paul, Minn., having a part number LC 220-04. It would be within the scope of the invention to provide each of delivery and return tubes 52 and 53 with foam tube insulation, in substantially the same manner described with respect to the foam tube insulation 42 of FIG. 5.

The cold therapy system of the present invention having been described in detail, its manner of operation may now be set forth. Reference is first made to FIG. 1. As a first step, the user releases storage strap 49 and uncoils tubing assembly 6. The female and male couplings 40 and 54 of delivery tubes 27 and 52 may be joined together. In a similar fashion, the female coupling 41 and male coupling 55 of return tubes 29 and 53 may also be joined together so that the pad 7 is properly connected to the system.

With the tube assembly 6 removed from cooler 2, the cooler handle 10 can be lowered as shown in FIG. 3 and the cooler lid 9 can be pivoted to its open position. At this stage, the reservoir bag 11 is filled with water and ice. The open top of reservoir bag 11 is thereafter rolled so as to close it, and is maintained in a closed position by drawstring 16 and its slide cord lock 18. Care must be taken to introduce sufficient water so that outlet tubing flange 14, which is connected to the inlet of pump 4, is covered during operation. The use of the reservoir bag within cooler 2 has a number of advantages. First of all, when the top portion of the bag is rolled to a closed condition and maintained in a closed position by drawstring 16, the chances of inadvertent and undesired spillage are greatly reduced. In addition, the air space between the inside surfaces of cooler 2 and the reservoir bag 11 provide additional thermal insulation. Since this system requires a minimum amount of water, more ice can be employed. With more ice and a minimal amount of water, cold temperatures last longer.

Since pump 4 is mounted within pump housing 3, externally of cooler 2, heat generated by the pump will be outside the cooler. Pump 4 is mounted in a floating fashion within pump housing 3 and is surrounded by the foamed material 31. It will be remembered that the foam material 31 serves as an insulator against both noise and heat generated by the pump. Operation of the pump is further quieted by the segments of gum rubber tubing 23 and 25. Since the pump is mounted within pump housing 3, externally of cooler 2, there is no set up or necessary tube connection with respect to the pump. External positioning of the pump also assures that the lid 9 of cooler 2 may be closed during operation. Having filled the reservoir bag 11 with water and ice, the user can close the cooler lid and connect the power supply jack 37 to the socket 38 in pump housing 3. The power supply 36 can thereafter be plugged into an ordinary wall socket and the pump can be started by shifting the manual element of switch 33 from its "STOP" position to any desired one of its three "ON" positions.

In the cold therapy system of the present invention, temperature of the water circulating through pad 7 is controlled by the flow rate. Pump 4 has a variable-speed motor. At the highest speed, the water flow will be coldest, falling within the range of from about 38° to about 45° F. At the intermediate motor speed, the flowing water will have a temperature of from about 40° to about 50° F. At the lower speed of the pump, the flowing water will have a temperature falling within the range of from about 45° to about 55° F. The temperature of the flowing water can be checked by the user at any time, by shifting the insulative member 48 to its retracted position, exposing temperature indicator 47. This in-line liquid crystal temperature indicator gives a reading of the water flow as it exits pad 7.

To complete the operation, the pad 7 is placed against or wrapped about that body part to be treated, and the cold therapy treatment is continued for the desired length of time. At the end of the cold therapy treatment, the pump is turned to "STOP" at switch 34. The power pack 36 is disconnected from the wall outlet and the power pack jack 37 is removed from socket 38. The pad 7 is disconnected from tube assembly 6 at the male and female couplings 40/54 and 41/55. Little or no leakage will occur at the female couplings 40 and 41 since they each have an internal shut-off mechanism. The cooler lid 9 is opened and the reservoir bag 11 is drained of ice and water. Cooler lid 9 is then pivoted to its closed position and the cooler handle is shifted to its upright position, as shown in FIG. 1. Thereafter, the hose assembly 6 is coiled about the cooler handle 10 in the manner shown in FIG. 1, and is maintained in position by storage strap 49.

Figure 6:
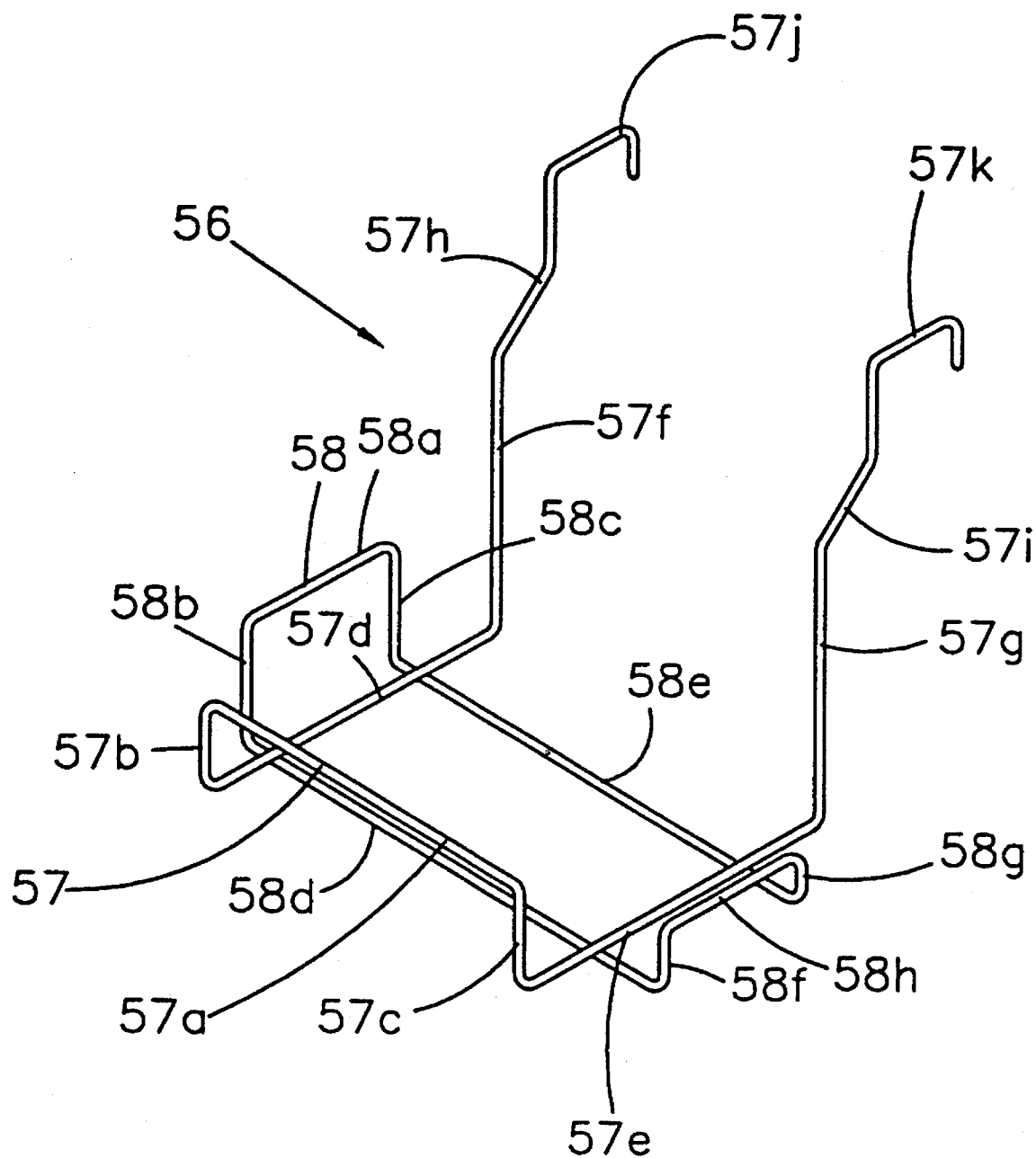
FIG. 6 is a perspective view of a support bracket for the cold therapy system of the present invention.

In some instances it may be desirable to support the cold therapy system of the present invention on a bed frame or the like. This can be accomplished by providing a support bracket of the type generally indicated at 56 in FIG. 6. The bracket is formed of two wire elements 57 and 58, welded together. Wire element 58 is formed in such a way as to have a longitudinal portion 57a. The longitudinal portion 57a terminates in a pair of downwardly depending vertical portions 57b and 57c. Vertical portions 57b and 57c, in turn, terminate in horizontal transverse portions 57d and 57e, respectively. Transverse portions 57d and 57e terminate in upturned, vertical portions 57f and 57g. Portions 57f and 57g are followed, respectively, by angular segments 57h and 57i. The wire segments 57h and 57i slope rearwardly and upwardly at an angle of about 45° to the horizontal. The uppermost ends of wire segments 57h and 57i terminate in a pair of identical hook-shaped segments 57j and 57k, respectively.

The wire member 58 is formed into a continuous loop made up of rectilinear segments. The ends (not shown) of wire member 58 are abutted and welded together. Wire member 58 has a first horizontal transversely extending portion 58a terminating in downwardly depending vertical segments 58b and 58c. Segments 58b and 58c terminate in longitudinally extending horizontal portions 58d and 58e, respectively. Segments 58d and 58e terminate in vertical upwardly directed segments 58f and 58g, both of which terminate in the horizontal, transversely extending segment 58h.

The entire bracket 56 may be made, for example, of No. 3 steel wire. Wire members 57 and 58 are welded together at those four points where they contact each other. The entire structure 56 may be coated with an appropriate material such as nylon.

Hook-like segments 57j and 57k are so dimensioned as to fit over a horizontal member of a conventional bed frame. When the cooler 2 is placed in bracket 56, it will rest upon the horizontal transverse segments 57d and 57e of wire member 57. The cooler 2 will be precluded from transverse movement by the upstanding wire segments 57f and 57g of wire member 57 adjacent one longitudinal side of the cooler and by wire segments 57a, 57b and 57c adjacent the opposite longitudinal side of the cooler. Longitudinal movement of the cooler is precluded by the upstanding portion of wire member 58 comprising segments 58a, 58b and 58c at one end of the cooler and by the upstanding portion of wire member 58 constituting segments 58f, 58g and 58h at the other end of the cooler. It will be noted that segments 58f and 58g of wire member 58 are shorter than segments 58b and 58c. This enables the wire segment 58h of wire member 58d to be located below the pump housing 3 affixed to the end 19 of cooler body 8.

The sloped wire segments 57h and 57i form an offset between the hook-like segments 57j and 57k and the vertical segments 57f and 57g. This enables the lid 9 of cooler 2 to be shifted to its open position, while resting in bracket 56. This offset will also accommodate handle 10 in its horizontal position.

Modifications may be made in the invention without departing from the spirit of it.

What is claimed:

1. A cold therapy system for cooling an area of the user's body, the system comprising a portable reservoir for water and ice, said reservoir comprising a portable cooler made of insulative material and having a bottom, side walls and an openable lid, said reservoir having an inlet port and an outlet port, a pump, said pump having an inlet and an outlet, a waterproof pad, an inlet and an outlet for said pad, a water path through said pad connecting said pad inlet and said pad outlet, means connecting said reservoir outlet to said pump inlet, a delivery tube connecting said pump outlet and said pad inlet, a return tube connecting said pad outlet and said reservoir inlet, a housing for said pump, said pump being mounted within said housing, said pump housing being affixed to an exterior surface of one of said reservoir walls, whereby the water and ice of said reservoir is insulated from heat generated by said pump by the insulative wall of the reservoir to which the pump housing is affixed.

2. The system claimed in claim 1 wherein said delivery and return tubes are insulated, a liquid crystal temperature indicator located within one of said insulated delivery and return tubes, said insulation of said one of said tubes containing said temperature indicator being shiftable between a normal position covering said portion of said last mentioned tube containing said temperature indicator and a retracted position exposing said temperature indicator to view.

3. The system claimed in claim 2 wherein said liquid crystal temperature indicator is located within said return tube.

4. The system claimed in claim 1 including a variable-speed electric motor comprising a part of said pump, a control circuit and a four-position switch for said pump motor, said switch having a motor-stop position and three motor-on positions for high, medium and low motor speeds, whereby to control the rate of water flow through said system and thus the temperature of said pad.

5. The system claimed in claim 1 wherein said pump is wrapped with foam material within said pump housing for heat and noise insulation and is supported within said housing primarily by said connections to said pump inlet and said pump outlet.

* * * * *